United States Patent
Kang et al.

(10) Patent No.: US 9,620,325 B2
(45) Date of Patent: *Apr. 11, 2017

(54) CT DEVICES AND METHODS THEREOF

(71) Applicants: TSINGHUA UNIVERSITY, Beijing (CN); NUCTECH COMPANY LIMITED, Beijing (CN)

(72) Inventors: Kejun Kang, Beijing (CN); Chuanxiang Tang, Beijing (CN); Ziran Zhao, Beijing (CN); Zhe Zhang, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/758,768

(22) PCT Filed: Oct. 31, 2013

(86) PCT No.: PCT/CN2013/086286
§ 371 (c)(1),
(2) Date: Jun. 30, 2015

(87) PCT Pub. No.: WO2014/101566
PCT Pub. Date: Jul. 3, 2014

(65) Prior Publication Data
US 2015/0340192 A1    Nov. 26, 2015

(30) Foreign Application Priority Data

Dec. 31, 2012 (CN) .......................... 2012 1 0593844
Jan. 28, 2013 (CN) .......................... 2013 1 0032020

(51) Int. Cl.
*A61B 6/00* (2006.01)
*H01J 35/14* (2006.01)
(Continued)

(52) U.S. Cl.
CPC .............. *H01J 35/14* (2013.01); *A61B 6/032* (2013.01); *A61B 6/4028* (2013.01);
(Continued)

(58) Field of Classification Search
USPC ...................................................... 378/4, 10
See application file for complete search history.

(56) References Cited

U.S. PATENT DOCUMENTS

| | | |
|---|---|---|
| 4,352,021 A | 9/1982 | Boyd et al. |
| 6,990,171 B2 | 1/2006 | Toth et al. |

(Continued)

FOREIGN PATENT DOCUMENTS

| | | |
|---|---|---|
| CN | 101266217 A | 9/2008 |
| CN | 101352353 A | 1/2009 |

(Continued)

OTHER PUBLICATIONS

International Patent Application No. PCT/CN2013/086287; Int'l Search Report; dated Jan. 30, 2014; 4 pages.

(Continued)

*Primary Examiner* — Nicole Ippolito
*Assistant Examiner* — Hanway Chang
(74) *Attorney, Agent, or Firm* — Baker & Hostetler LLP

(57) ABSTRACT

CT Devices and methods thereof are disclosed. The CT device comprises an electron beam generation unit, a circular reflection target (9) and a circular detector array. The electron beam generation unit comprises an electron gun (7), a deflection scanning unit and a restrictor (16), wherein the electron gun (7) generates electron beams, the deflection scanning unit deflects the electron beams with a deflection direction varying as time so as to implement a circular scanning, and the restrictor (16) has a plurality of circularly distributed holes, and wherein when the electron beams scan along the circularly distributed holes, a plurality of electron (Continued)

beams that are distributed circularly are output. The circular reflection target (9) is disposed to be coaxial with the circularly distributed electron beams, wherein the circularly distributed electron beams bombard the circular reflection target (9) to generate X-rays that intersect the axis of the circularly distributed electron beams. The circular detector array (11) is disposed to be coaxial with the circular reflection target and includes a plurality of detection units which receive the X-rays after they have passed through an object to be detected (10).

14 Claims, 6 Drawing Sheets

(51) Int. Cl.
*H05G 1/10* (2006.01)
*G01N 23/04* (2006.01)
*A61B 6/03* (2006.01)

(52) U.S. Cl.
CPC ......... *A61B 6/4275* (2013.01); *G01N 23/046* (2013.01); *H05G 1/10* (2013.01); *F04C 2270/041* (2013.01); *G01N 2223/419* (2013.01)

(56) References Cited

U.S. PATENT DOCUMENTS

| | | |
|---|---|---|
| 2003/0169849 A1 | 9/2003 | Smyth |
| 2008/0169961 A1 | 7/2008 | Steinway et al. |
| 2008/0277591 A1 | 11/2008 | Shahar et al. |
| 2010/0303198 A1 | 12/2010 | Hampel |
| 2015/0342013 A1* | 11/2015 | Kang ............... H01J 35/06 378/4 |

FOREIGN PATENT DOCUMENTS

| | | |
|---|---|---|
| CN | 101405619 A | 4/2009 |
| CN | 101573157 A | 11/2009 |
| CN | 101576513 A | 11/2009 |
| CN | 102106740 A | 6/2011 |
| CN | 102448376 A | 5/2012 |
| CN | 102645442 A | 8/2012 |
| CN | 203083952 U | 7/2013 |
| CN | 203178216 U | 9/2013 |
| DE | 102007036038 A1 | 2/2009 |
| JP | 2012-034901 A | 2/2012 |
| WO | WO 2009/092372 A1 | 7/2009 |

OTHER PUBLICATIONS

European Patent Application No. 13869644.8; Extended Search Report; dated Aug. 1, 2016; 7 pages.

* cited by examiner

CT DEVICES AND METHODS THEREOF

CROSS-REFERENCE TO RELATED APPLICATIONS

This application is the National Stage of International Application No. PCT/CN2013/086286, filed on Oct. 31, 2013, entitled "CT DEVICE AND METHOD THEREOF," which claims priority to Chinese Patent Application No. 201310032020.2 filed on Jan. 28, 2013 and Chinese Application No. 201210593844.2 filed on Dec. 31, 2012, the disclosures of which are incorporated herein by reference in their entireties.

TECHNICAL FIELD

The present technique generally relate to the fields of medical imaging, industry detection and others. The technique may be directly applied to medial field that needs ultra-fast imaging, and also applied to industry field, such as non-destructive detection field.

BACKGROUND

CT, short for Computed Tomography, denotes a scanning technique to use a computer system to reconstruct a CT image of an object under detection, so as to obtain a three-dimension CT image. The scanning technique is to have rays of a single axial plane pass through the object under detection, collect transmitted rays by a computer system and reconstruct an image by a three-dimension reconstruction approach, where different parts of the object under detection have different absorptivities and transmissivities to the transmitted rays. The term "CT" used herein, if not specified otherwise, refers to an X-ray CT.

CT technique has five generations according to its development. The first four generations have a scanning part that can be implemented by a movable X-ray tube and a detector (mechanical scanning mode). The third generation and the fourth generation use a spiral scanning mode, and the scanning part used therein is comprised of a X-ray tube, a detector and a scanning stand on which the X-ray tube and the detector are mounted. In operation, the X-ray tube emits X-rays to an object to be scanned from periphery of the object by moving the scanning stand at a high speed, and a scanned CT image can be obtained after reception of the detector and processing of a computer system.

The spiral Multi-detector row CT (MDCT) that comes out in the recent years substantially belongs to the fourth generation CT, and has a scanning speed that is nearly the same as the spiral single-detector row CT. The rows of detectors, however, are increased, and thus multi-row data may be obtained by rotating the X-ray rube for one round. As for the well-developed MDCT of 64 rows, it needs 0.33 s to rotate for one round, and the temporal resolution is better than 50 ms (the temporal resolution mainly depends on the scanning period, and also on the scanning coverage and the reconstruction approach in the MDCT).

The foregoing fourth generation CT has an advantage of a high spatial resolution, but it also has a disadvantage of a low temporal resolution. The main factor that limits the temporal resolution is its scanning speed. As for the most advanced spiral MDCT, the maximal scanning speed is only 0.33 s/round, which depends on the mechanical strength limit of the scanning stand and the X-ray tube. When the CT rotates at a high speed, the line speed of the X-ray rube may be up to the first cosmic velocity. In order to ensure the stability of the structure, the rotation speed of the CT has a limit.

The fifth generation CT (UFCT) has a different scanning principle from the first four generations. An advanced electron beam technology is used to generate X-rays. The anode and cathode of the bulb tube are separate. Electron beams are emitted from the electron gun at the cathode, and are accelerated to form high-energy electron beams, which pass through a focusing and magnetic deflection coil, and project on the target surface of the anode which has a form of a 210° arc, and then X-ray beams are generated. Comparing with the conventional mechanical rotation, the scanning speed may be up to 50 ms/round.

In the medical imaging application, take the heart imaging as an example. If the mechanical scanning mode is used, one position will be scanned for 2 or 3 times within one second. If the electron beam scanning mode is used, one position will be scanned for 20 times within one second. In the industry detection application, the scanning time of performing CT on a large-scale object generally is several minutes.

In the existing CT imaging devices, there are three ways to increase the scanning speed: 1. Enhance hardware performance. For example, enhance the rotation speed of the mechanical structure, increase the number of ray sources, and others. 2. Perform equivalent scanning by means of the stability of the object to be detected. For example, the gating technique is used in the heart imaging. 3. Change the scanning mode to, for example, electron beam scanning (UFCT).

All the means may speed up the scanning speed to a certain extent, but cannot achieve ultra-fast scanning and CT imaging on an object that moves at a high speed.

SUMMARY

In view of the limit on the scanning speed (i.e., the temporal resolution) of the prior CT techniques, an object of the present technique is to provide a CT device of a high temporal resolution.

According to embodiments, there is provided a CT device comprising an electron beam generation unit that comprises an electron gun, a deflection scanning unit and a restrictor, wherein the electron gun generates electron beams, the deflection scanning unit deflects the electron beams with a deflection direction varying as time so as to implement a circular scanning, and the restrictor has a plurality of circularly distributed holes, and wherein when the electron beams scan along the circularly distributed holes, a plurality of electron beams that are distributed circularly are output; a circular reflection target which is disposed to be coaxial with the circularly distributed electron beams, wherein the circularly distributed electron beams bombard the circular reflection target to generate X-rays that intersect the axis of the circularly distributed electron beams; and a circular detector array which is disposed to be coaxial with the circular reflection target and configured to include a plurality of detection units which receive the X-rays after they have passed through an object to be detected.

According to embodiments, the CT device may further comprise a resonance acceleration cavity configured to operate in TM010 mode to receive electron beams emitted from the electron beam generation unit and accelerate the received electron beams.

According to embodiments, the CT device may further comprise a coupler and a microwave power source, wherein the coupler feeds microwaves generated from the microwave power source to the resonance acceleration cavity to accelerate the electron beams.

According to embodiments, the electron beam generation unit may further comprise a driving mechanism configured to drive the restrictor to move to and fro a certain degree when the electron beam generation unit generates electron beams, the degree being less than or equal to the angle between two lines, one line connecting one of the holes on the restrictor to a center of a circle on which the circularly distributed holes are positioned, the other line connecting an adjacent hole to the center.

According to embodiments, the CT device may further comprise a circular cowling disposed at the front of the circular reflection target and having holes corresponding to the plurality of electron beams, to restrict beam spots of the electron beams on the circular reflection target.

According to embodiments, the CT device may further comprise a drift stage disposed between the resonance acceleration cavity and the circular reflection target and configured to cause the electron beams to self focus.

According to embodiments, the CT device may further comprise a transmission unit configured to carry the object to be detected to move along the axis of the circular detector array.

According to embodiments, the angle between the normal of the target surface of the circular reflection target and the incident direction of the electron beams is larger than 90 degrees.

According to embodiments, the CT device may further comprise a collimator configured to collimate the X-rays.

According to embodiments, each detection unit in the circular detector array is a multi-detector row unit.

According to another aspect, there is provided a method of a CT device comprising steps of generating electron beams from an electron gun; deflecting the electron beams with a deflection direction varying as time so as to implement a circular scanning; restricting the electron beams by a restrictor that has a plurality of circularly distributed holes, so that when the electron beams scan along the circularly distributed holes, a plurality of electron beams that are distributed circularly are output; generating X-rays that intersect an axis of the circularly distributed electron beams by the electron beams bombarding the circular reflection target; and detecting X-rays that have passed through an object to be detected.

According to some embodiments, the method may further comprise a step of accelerating the circularly distributed electron beams in sequence by a resonance acceleration cavity that operates in TM010 mode.

According to some embodiments, the method may further comprise a step of feeding, by a coupler, microwaves generated by a microwave power source to the resonance acceleration cavity to accelerate the electron beams in sequence.

According to some embodiments, the method may further comprise a step of driving the restrictor to move to and fro a certain degree when generating the electron beams, the degree being less than or equal to the angle between two lines, one line connecting one of the holes on the restrictor to a center of a circle on which the circularly distributed holes are positioned, the other line connecting an adjacent hole to the center.

According to the solutions above, it can improve the CT scanning speed drastically while ensuring a certain temporal resolution.

BRIEF DESCRIPTION OF THE DRAWINGS

The implementations of the present technique are illustrated in the drawings. The drawings and implementations provide some embodiments of the present technique non-exclusively without limitation, where.

DETAILED DESCRIPTION OF THE EMBODIMENTS

Figure 1:
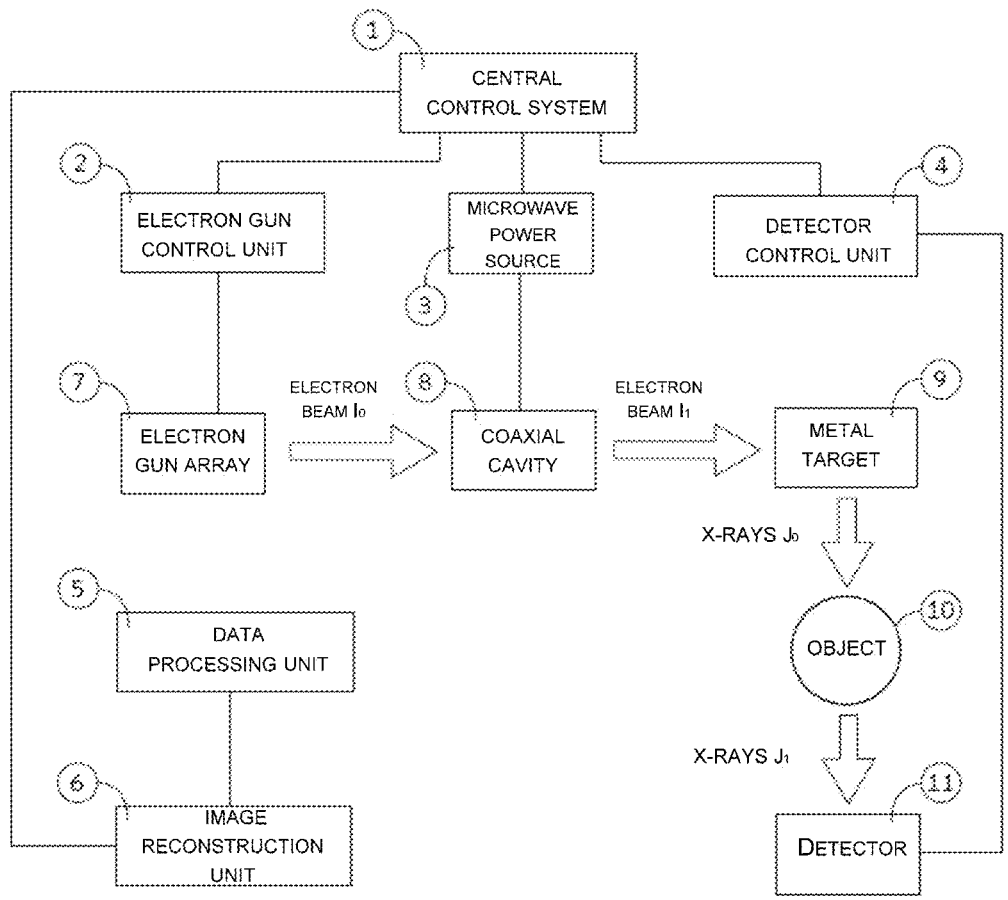
FIG. 1 illustrates a general view of a CT device according to an embodiment of the present technique.

The particular embodiments of the present technique are described below in details. It shall be noted that the embodiments herein are used for illustration only, but not limiting the present technique. In the description below, a number of particular details are explained to provide a better understanding to the present technique. However, it is apparent to those skilled in the art the present technique can be implemented without these particular details. In other examples, well known circuits, materials or methods are not described so as not to obscure the present technique.

Throughout the specification, the reference to "one embodiment," "an embodiment," "one example" or "an example" means that the specific features, structures or properties described in conjunction with the embodiment or example are included in at least one embodiment of the present technique. Therefore, the phrases "in one embodiment," "in an embodiment," "in one example" or "in an example" occurred at various positions throughout the specification may not refer to one and the same embodiment or example. Furthermore, specific features, structures or properties may be combined into one or several embodiments or examples in any appropriate ways. Moreover, it should be understood by those skilled in the art that the term "and/or" used herein means any and all combinations of one or more listed items.

In order to further improve the scanning speed of a CT device, according to an embodiment, there is provided a CT device comprising an electron beam generation unit that comprises an electron gun, a deflection scanning unit and a restrictor, wherein the electron gun generates electron beams, the deflection scanning unit deflects the electron beams with a deflection direction varying as time so as to implement a circular scanning, and the restrictor has a plurality of circularly distributed holes, and wherein when the electron beams scan along the circularly distributed holes, a plurality of electron beams that are distributed circularly are output; a circular reflection target which is disposed to be coaxial with the circularly distributed electron beams, wherein the circularly distributed electron beams bombard the circular reflection target to generate X-rays that intersect the axis of the circularly distributed electron beams; and a circular detector array which is disposed to be coaxial with the circular reflection target and configured to include a plurality of detection units which receive the X-rays after they have passed through an object to be detected.

For example, for a coaxial resonance cavity powered by a radio frequency microwave power source of a high repetition frequency, circularly distributed electron beams that are subjected to processing in the deflection scanning unit and the restrictor are used. The electron beams are accelerated in the TM010 field in the coaxial resonance cavity, drift and then bombard the reflection target to generate a sequence of X-rays that are perpendicular to the axis of the coaxial resonance cavity and pass through the same center. The sequence of X-rays is used to perform CT imaging on an object to be detected.

According to the embodiment that uses the foregoing structure, it may improve the scanning speed while ensuring a certain spatial resolution. Meanwhile, by adjusting the feed power of the microware power source, the energy of the X-rays may be adjusted in a range, giving a possibility of generating high-energy X-rays which are applicable to the industry non-destructive detection field. For example, X-ray beams of different energies may be generated by accelerating electron beams with different feed powers, and thus multi-energy scanning, for example, dual-energy scanning, can be implemented.

For example, it may output electron beams of different energies, i.e., X-rays of different energies, by adjusting the feed power of the microwave power source. In a certain range, the relation between electron beams and feed power satisfies:

$$E \propto \sqrt{P} \quad (1)$$

where E is the energy of the electron beam, and P is the feed power. Thus, it may output X-rays of multiple energies.

FIG. 1 illustrates a general view of a CT device according to an embodiment of the present technique. As shown in FIG. 1, the CT device according to the embodiment comprises an electrical scanning unit, a central control system 1, an electron gun control unit 2, a microwave power source 3, a detector control unit 4, a data processing unit 5 and an image reconstruction unit 6. The electrical scanning unit comprises an electron beam generation unit, coaxial resonance acceleration cavity 8, a metal target 9 and a circular detector 11. The electron beam generation unit comprises for example an electron gun 7, a horizontal and a vertical deflection coil (i.e., a deflection scanning unit) and a restrictor.

Figure 2:
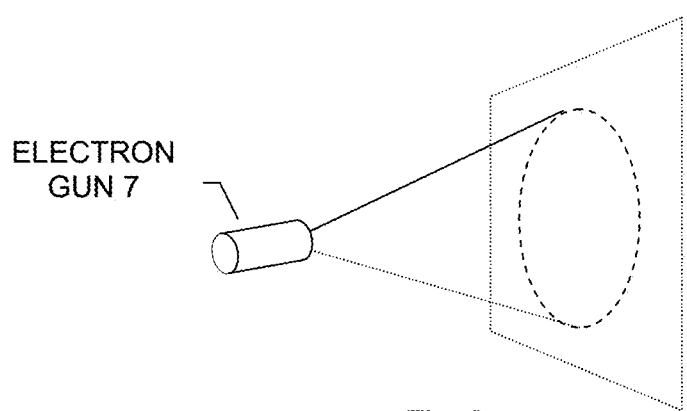
FIG. 2 illustrates a schematic diagram of an electrical scanning part of a CT device according to an embodiment of the present technique.

The electrical scanning unit is the hardware for implementing ultra-fast CT imaging. As shown in FIG. 2 which illustrates the structure of the electrical scanning unit, the electron gun 7 will emit electrons if triggered.

Figure 3:
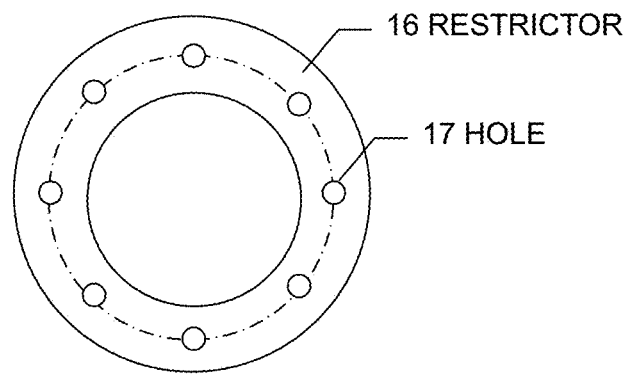
FIG. 3 illustrates a schematic diagram of a restrictor of a CT device according to an embodiment of the present technique.
Figure 4:
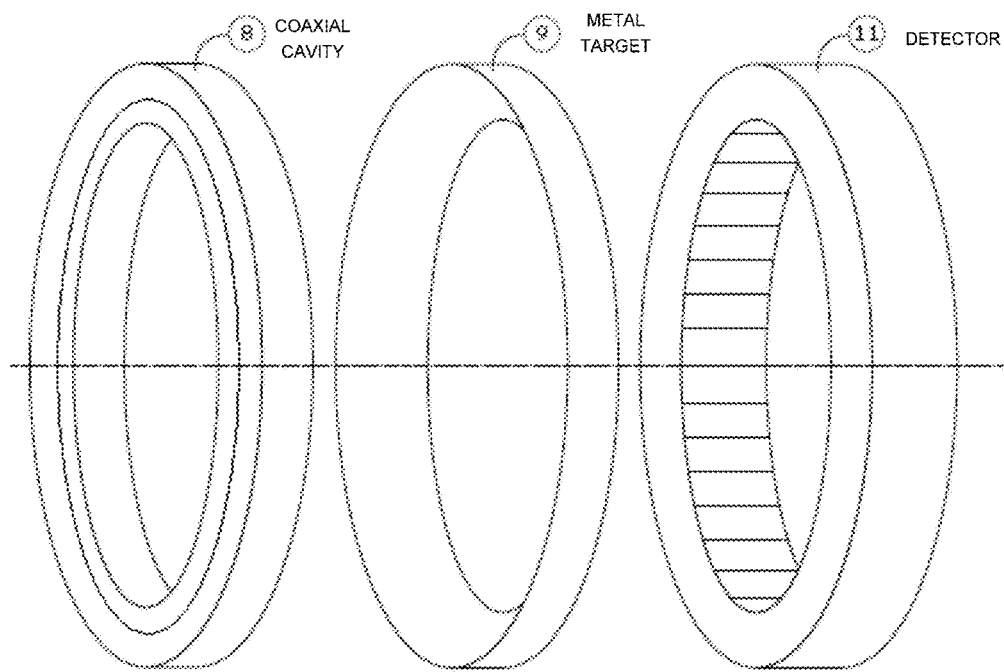
FIG. 4 illustrates an exploded view of an electrical scanning part of a CT device according to an embodiment of the present technique.

As shown in FIG. 2, the electron gun 7 generates electron beams which performs a circular scanning under the control of a deflection coil (by for example applying to a horizontal deflection coil and a vertical deflection coil sine signals that are different by 90° in phase, i.e., s sine signal and a cosine signal, respectively). FIG. 3 illustrates a restrictor of a CT device according to an embodiment of the present technique. The limier 16 is disposed downstream to the electron gun 7, and a deflection unit controls the electron beams to scan along holes that are distributed circularly on the restrictor 16. When electron beams scan to a hole 17, a part of the electron beams pass through it and form electron beams that are parallel to the axis. Although it is shown in FIG. 3 that the restrictor 16 has several holes, it is obvious to one skilled in the art that the restrictor may have more holes. For example, a metal plane on which hundreds of circularly distributed holes are formed may be used as the restrictor.

The coaxial resonance acceleration cavity 8 operates in TM010 mode, and accelerates electrons longitudinally to have the electrons bombard the metal target 9 to generate X-rays. The circular detector 11 receives X-rays that have passed through an object to be detected 10.

Figure 5:
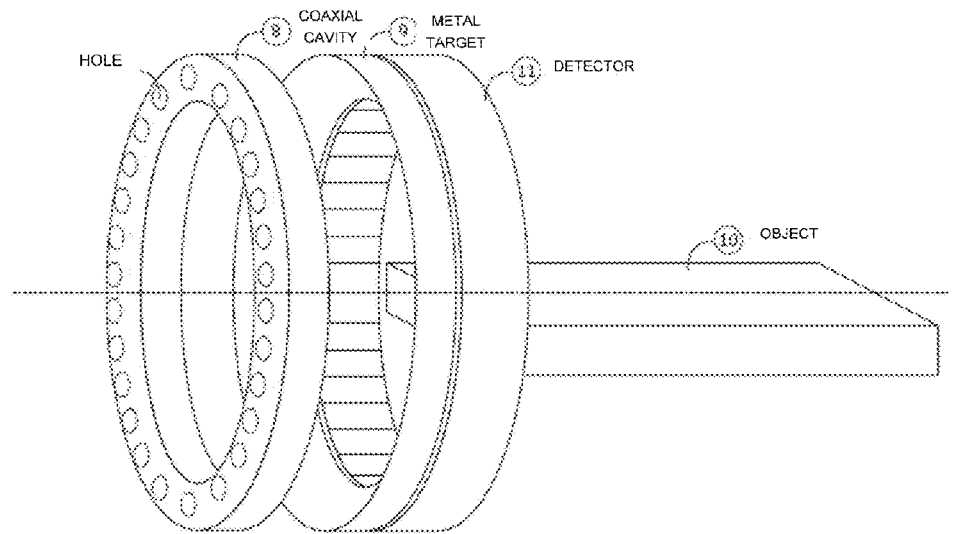
FIG. 5 illustrates a synthesis schematic diagram of an electrical scanning part of a CT device according to an embodiment of the present technique.

FIG. 5 illustrates relative positions of various members of the electrical scanning unit when it operates. The restrictor that restricts the electron beams generated by the electron gun 7 is arranged on a side of the coaxial cavity 8 that is away from the metal target 9. There is a drift stage between the coaxial cavity 8 and the metal target 9, to have the electron beams self focus. There is a small gap between the metal target 9 and the detector 11, where a collimator may be arranged to ensure the imaging quality.

In performing imaging, as shown in FIG. 1, the electron gun control unit 2 receives a scanning start command from the central control system 1, and controls the electron gun 7 to emit electron beams $I_0$ (according to the electron acceleration energy and design of the collimator, 1~3 electron guns are allowed to emit electrons at the same time to expedite the scanning speed). The electron beams $I_0$ are accelerated in the coaxial resonance acceleration cavity 8 to have expected energy (dependent on the feed power of the microware power source 3, and may be low to 100 keV, or be up to 1 MeV). The accelerated electron beams $I_1$ bombard the metal target 9 to generate X-rays $J_0$ that intersect the axis of the coaxial resonance cavity. For example, the X-rays are substantially perpendicular to the axis of the coaxial resonance cavity, collimated by the collimator between the metal target 9 and the detector 11, and pass through an object 10 to be detected that is carried on a transmission unit. The attenuated X-rays $J_1$ are received by the detector 11. The transmission unit moves along the axis of the coaxial resonance cavity.

The detector control unit 4 receives a scanning start instruction from the central control unit 1, and controls the detector 11 to collect data and transmit the data to the central control unit 1. The central control unit re-arranges the collected detector data according to the sequence of the electron beams that are restricted by the restrictor 16, and transmit the data to the data processing unit 5 for pre-processing. The data processing unit 5 performs processing such as non-uniformity correction, hardening correction, brightness correction, and so on, and transmits the processed standard projection data to the image reconstruction unit 6 for reconstruction, and thereby a sequence of CT images of specific positions of the object to be detected can be obtained.

Figure 6:
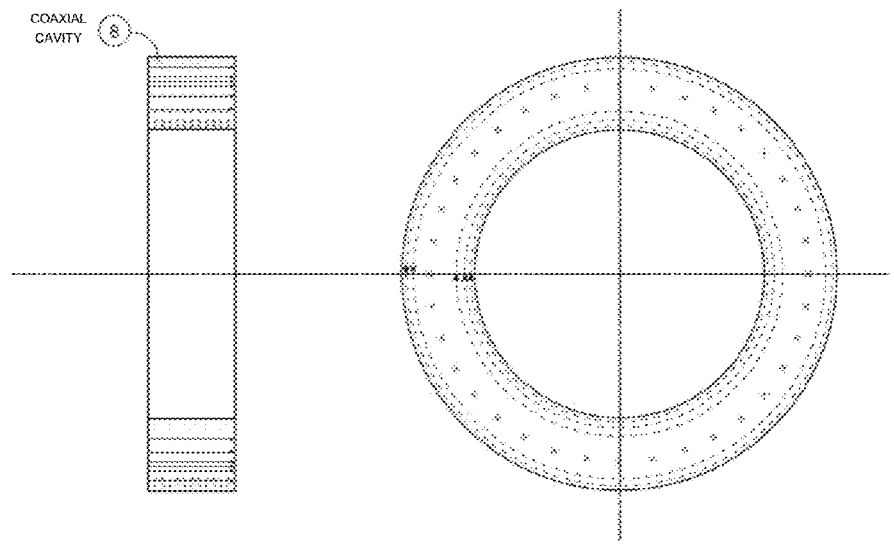
FIG. 6 illustrates a field pattern when a coaxial cavity operates in a CT device according to an embodiment of the present technique.

The acceleration principle of the coaxial resonance acceleration cavity 8 in the electrical scanning unit is described hereinafter. The coaxial resonance acceleration cavity 8 receives power from the microwave power source 3 when it operates, and establishes a field of TM010 mode in the cavity, as shown in FIG. 6. The left of FIG. 6 is a left view, the right of FIG. 6 is a front view, the dotted line denotes the magnetic field, and the solid line denotes the electrical field. The field distribution of the mode has the following attributes:

The electrical field has only longitudinal components, and the magnetic field has only axial components.

The longitudinal electrical field and the axial magnetic field are uniform along the longitudinal direction.

The longitudinal electrical field is maximal at a position that is about the middle point between the outer diameter and the inner diameter of the coaxial cavity and closer to the outer diameter.

The magnetic field is 0 at a position where the longitudinal electrical field is maximal (dependent on the attributes of the resonance cavity).

The TM010 mode of the coaxial cavity is suitable to accelerate electrons due to the foregoing field distribution attributes. Furthermore, the magnetic field that is nearly linear at about the position the electrical field is maximal causes the electron beams to self focus, and thus there is no requirement for a focusing module.

Figure 8:
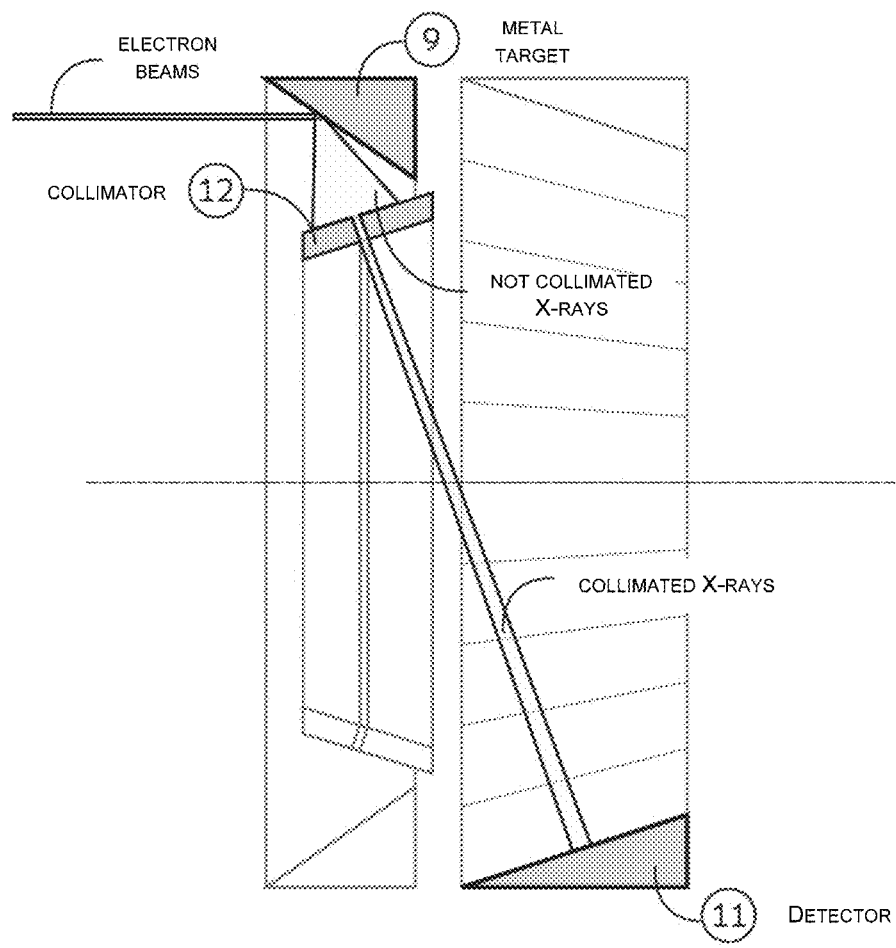
FIG. 8 illustrates a schematic diagram of a circular reflection target in a CT device according to an embodiment of the present technique.
Figure 10:
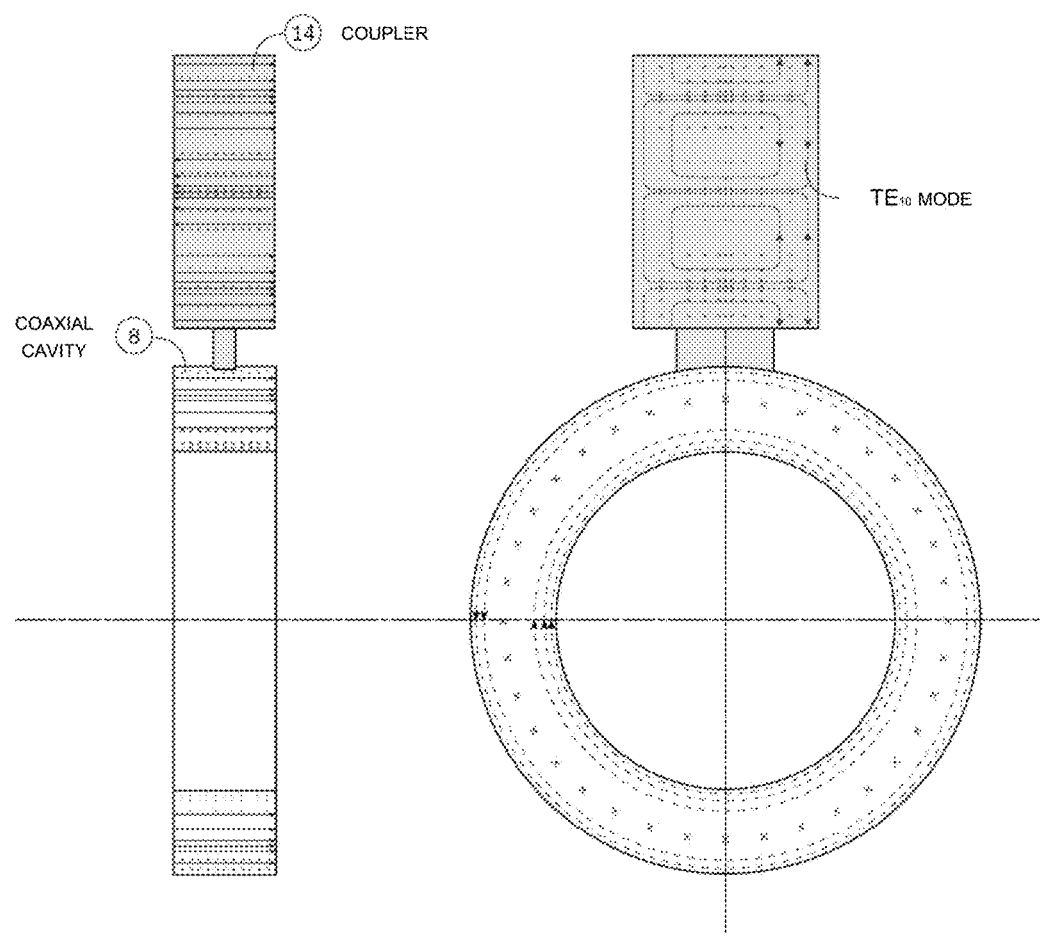
FIG. 10 illustrates a schematic diagram of a coaxial cavity and a coupler in a CT device according to an embodiment of the present technique.

Now refer to FIG. 10. The left of FIG. 10 is a right view of the coaxial cavity 8 and the coupler 14, and the right of FIG. 10 is the front view of the coaxial cavity 8 and the coupler 14. The field shown in FIG. 10 is the field pattern of the cross section of the longitudinal direction (vertical to the paper) of the view. In order to excite a field of TM010 mode in the coaxial cavity, the field pattern transmitted in the coupler (shown in gray in FIG. 10) must match the field pattern of the coaxial cavity. The lowest order mode in the waveguide coupler is TE10 mode, and such kind of field pattern may be established if the coupler is arranged as shown in FIG. 8. That is, the short side of the waveguide is parallel to the axis of the coaxial gravity, and the long side is perpendicular to the axis of the coaxial gravity. As can be seen from FIG. 10, the field pattern of the coupler matches the field pattern of the coaxial cavity, and thus a field of TM010 mode can be excited effectively in the coaxial cavity.

Figure 7:
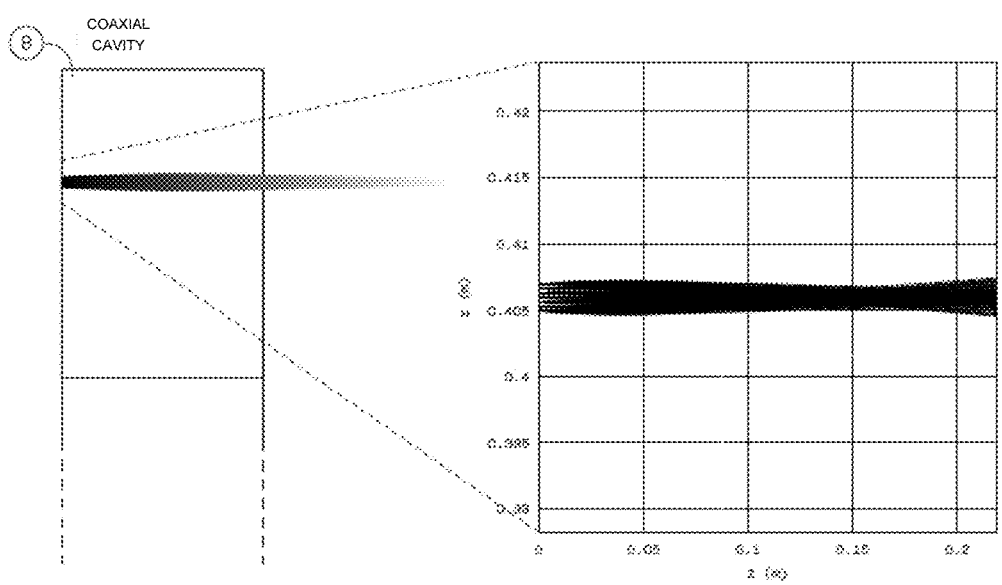
FIG. 7 illustrates a trajectory of electron beams when a coaxial cavity operates in a CT device according to an embodiment of the present technique.

The restrictor 16 may be arranged in the coaxial cavity 8 where the electrical field is maximal, and emits a bundle of electron beams with initial energy being about 10 keV. FIG. 7 shows a trajectory of electron beams that have typical parameters in the electromagnetic field in the coaxial cavity. The left of FIG. 7 is an enlarged left view of the coaxial cavity, and the right of FIG. 7 is an enlarged view of the electron beams. The coaxial cavity has a height of about 5 cm. As can be seen from the enlarged view of the trajectory of the electron beams at the right of FIG. 7 (only the part of a high electron density is shown and electrons that are not captured are filtered), the lateral size of the electron beams increases as the electron beams are accelerated in the coaxial cavity. However, in the drift stage following the coaxial cavity, a focusing effect appears due to the lateral momentum modulation inside the cavity. This is the reason to arrange a drift stage between the coaxial cavity 8 and the metal target 9. The drift stage may cause the electron beams to self focus.

In some embodiments, the metal target 9 and the detector 11 cannot be disposed at the same longitudinal position in the real installation, and thus the X-rays generated by bombardment of the electron beams arrive at the surface of the detector obliquely. Accordingly, it needs to incline the surface of the detector to have it perpendicular to the main incident direction of the X-rays.

Furthermore, in order to ensure the main incident direction of X-rays of the initial stage to be oblique, it needs to cause the angle between the normal of the target surface of the metal target and the incident direction of the electron beams larger than 90 degrees. Thus, the target surface of the metal target is oblique, as shown in FIG. 8. Preferably, the angle between the normal of the target surface of the metal target and the incident direction of the electron beams is about 135 degrees.

In some embodiments, in order to improve the quality of the X-rays irradiated on the object, it needs to arrange a collimator 12 between the metal target 9 and the detector 11. As shown in FIG. 8, the function of the collimator 12 is to block some X-rays of the initial stage (i.e., the X-rays generated during the bombardment of the electrons), and allow X-rays of the initial stage at the center to pass, so that the directionality of the X-rays is enhanced, and the interference of the angular distribution of the strength of the X-rays on the data accuracy if a multi-detector row unit is used is reduced.

In some embodiments, there is still some angular distribution of the strength of the X-rays even if a collimator 12 is arranged. The angular distribution can be used to achieve the purpose that images of a plurality of rows are scanned with one round. The term "multi-detector row unit" used herein means that detectors are grouped in multiple rows. When X-rays irradiates on the surfaces of the detectors, detectors of different rows sense X-rays of different strength (i.e., carrying information of different slices of the object), and thereby data of multiple slices of the object can be obtained. After scanning the object for one round, image of the multiple slices can be obtained. Therefore, the multi-detector row unit can shorten the total scanning time.

In the embodiment as shown, a coaxial resonance cavity is used to accelerate electron beams. In other embodiments, it may use a high-voltage electrical field, rather than a coaxial resonance cavity, to accelerate electron beams. Alternatively, in some embodiments, if the electron beams generated by the electron beam emission unit have enough strength, acceleration means is not necessary.

Figure 9:
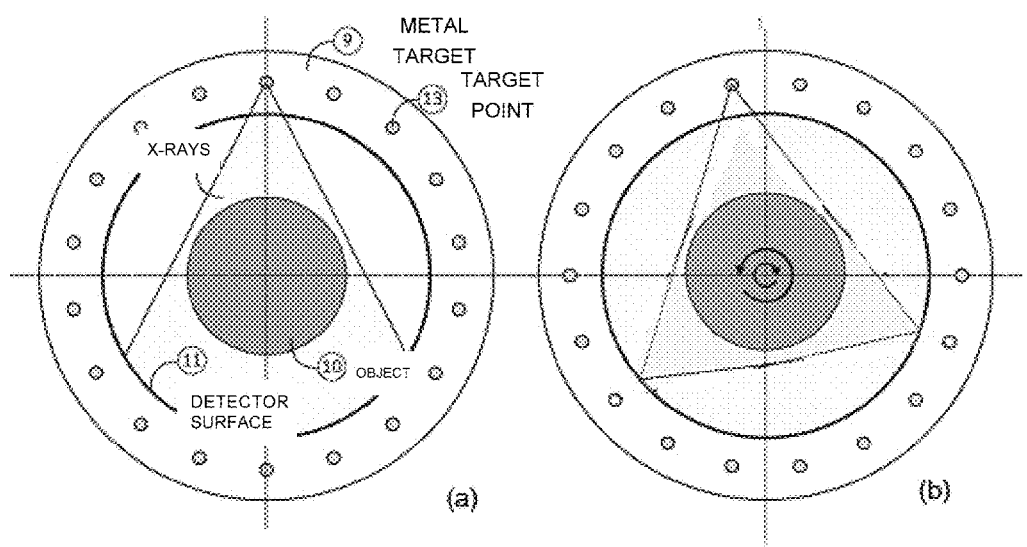
FIG. 9 illustrates a diagram of operation modes of a CT device according to an embodiment of the present technique.

In some embodiments, the CT device operates in more than one operation mode. It depends on the structure of the electron source, which is also an advantage of the CT device according to the present technique over the other CT devices. As shown in FIG. 9, (a) illustrates a common mode where the restrictor 16 restricts the continuous electron beams generated from the electron gun 7 along a circular trajectory. The electron beams bombard the metal target 9 and then X-rays are emitted from the target point 13, which pass through the object and are then received by the detector 11 to obtain data.

In some embodiments, a driving mechanism is provided to drive the restrictor 16 to wriggle. FIG. 9 depicts another operation mode in (b), i.e., the wriggle mode of the restrictor. The term "wriggle" means that the circle where the restrictor 16 is located move to and fro a certain small degree. The mode has an advantage of improving spatial resolution. The target point rotates along with the restrictor 16, and thus the emitted X-rays now may cover a range where the previous X-rays cannot cover otherwise. From that point of view, the "wriggle" of the restrictor 16 makes the density of the electron beams double. For example, "wriggling" in the mode as shown in (b) makes the density of the electron beams double. The more the times of the electron emission during "wriggle" is, the more the density is, and the higher the spatial resolution of the CT device is.

For example, in some embodiments, a driving mechanism is provided to drive the restrictor 16 to move to and fro a certain degree when the electron beam generation unit generates electron beams, the degree being less than or equal to the angle between two lines, one line connecting one of the holes on the restrictor to a center of a circle on which the circularly distributed holes are positioned, the other line connecting an adjacent hole to the center.

What shall be noted is that although the present technique is mainly applicable to the medical imaging, it is possible to apply it to the medical treatment or non-destructive detection field that require high energy X-rays due to the adjustment of the energy of X-rays.

Although an electron gun is used to generate electron beams that achieve a circular scanning and a restrictor 16 is used to restrict the electron beams to generate electron beams that are parallel to the axis in the embodiment, other electron beam generation units are also possible.

Figure 11:
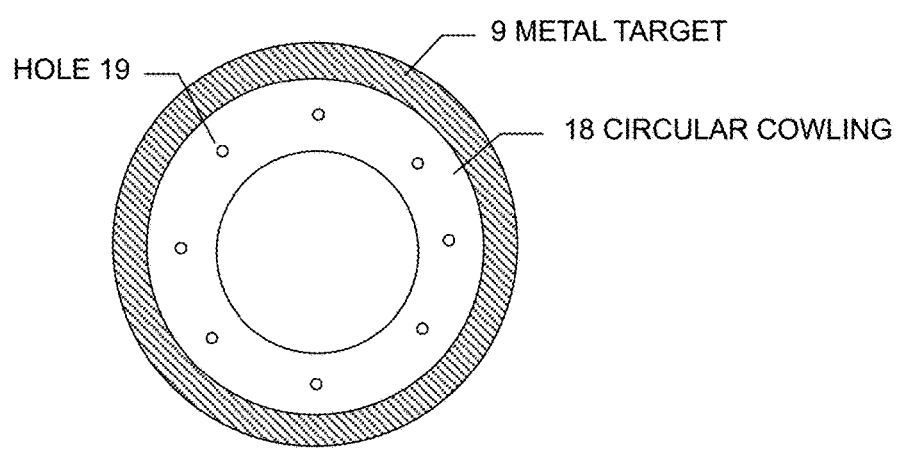
FIG. 11 illustrates a diagram of a circular cowling disposed in front of a reflection target in a CT device according to an embodiment of the present technique.

According to other embodiments, in order to reduce the size of the target point of the electron beams on the metal target 9 so as to enhance the spatial resolution of the CT device, a circular cowling 18 may be provided in front of the metal target. As shown in FIG. 11, the circular cowling has for example small holes to restrict the target point of the parallel electron beams from the restrictor 16 on the metal target 9. According to other embodiments, a high-voltage uniform electrical field may be provided between the restrictor 16 and the metal target 9 to accelerate the electron beams from the restrictor 16.

Although in the embodiment, examples of the generation of parallel electron beams, of acceleration, and of arrangement of the metal target are described, it is obvious to one skilled in the art that other embodiments can be formed by combining those examples, which are not described herein in details.

In some embodiments, there is provided a method of a CT device comprising steps of generating electron beams from an electron gun; deflecting the electron beams with a deflection direction varying as time so as to implement a circular scanning; restricting the electron beams by a restrictor that has a plurality of circularly distributed holes, so that when the electron beams scan along the circularly distributed holes, a plurality of electron beams that are distributed circularly are output; generating X-rays that intersect an axis of the circularly distributed electron beams by the electron beams bombarding the circular reflection target; and detecting X-rays that have passed through an object to be detected.

According to some embodiments, the method may further comprise a step of accelerating the circularly distributed electron beams in sequence by a resonance acceleration cavity that operates in TM010 mode.

According to some embodiments, the method may further comprise a step of feeding, by a coupler, microwaves generated by a microwave power source to the resonance acceleration cavity to accelerate the electron beams in sequence.

According to some embodiments, the method may further comprise a step of driving the restrictor to move to and fro a certain degree when generating the electron beams, the degree being less than or equal to the angle between two lines, one line connecting one of the holes on the restrictor to a center of a circle on which the circularly distributed holes are positioned, the other line connecting an adjacent hole to the center.

The foregoing detailed description has set forth various embodiments of the CT device and method of the same via the use of block diagrams, flowcharts, and/or examples. Insofar as such block diagrams, flowcharts, and/or examples contain one or more functions and/or operations, it will be understood by those skilled in the art that each function and/or operation within such examples may be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, may be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of those skilled in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communications link, a wireless communication link, etc.).

While the present technique has been described with reference to several typical embodiments, it is apparent to those skilled in the art that the terms are used for illustration and explanation purpose and not for limitation. The present technique may be practiced in various forms without departing from the esprit or essence of the present technique. It should be understood that the embodiments are not limited to any of the foregoing details, and shall be interpreted broadly within the esprit and scope as defined by the following claims. Therefore, Modifications and alternatives falling within the scope of the claims and equivalents thereof are to be encompassed by the scope of the present technique which is defined by the claims as attached.

What is claimed is:

1. A CT device comprising
an electron beam generation unit that comprises an electron gun, a deflection scanning unit and a restrictor, wherein the electron gun generates electron beams, the deflection scanning unit deflects the electron beams with a deflection direction varying as time so as to implement a circular scanning, and the restrictor has a plurality of circularly distributed holes, and wherein when the electron beams scan along the circularly distributed holes, a plurality of electron beams that are distributed circularly are output;
a circular reflection target disposed to be coaxial with the circularly distributed electron beams, wherein the circularly distributed electron beams bombard the circular reflection target to generate X-rays that intersect the axis of the circularly distributed electron beams; and
a circular detector array disposed to be coaxial with the circular reflection target and configured to include a plurality of detection units which receive the X-rays after they have passed through an object to be detected.

2. The CT device according to claim 1, further comprising a resonance acceleration cavity configured to operate in TM010 mode to receive electron beams emitted from the electron beam generation unit and accelerate the received electron beams.

3. The CT device according to claim 2, further comprising a coupler and a microwave power source, wherein the coupler feeds microwaves generated from the microwave power source to the resonance acceleration cavity to accelerate the electron beams.

4. The CT device according to claim 1, wherein the electron beam generation unit further comprises a driving mechanism configured to drive the restrictor to move to and fro a certain degree when the electron beam generation unit generates electron beams, the degree being less than or equal to the angle between two lines, one line connecting one of the holes on the restrictor to a center of a circle on which the circularly distributed holes are positioned, the other line connecting an adjacent hole to the center.

5. The CT device according to claim 1, further comprising a circular cowling disposed at the front of the circular reflection target and having holes corresponding to the plurality of electron beams, to restrict beam spots of the electron beams on the circular reflection target.

6. The CT device according to claim 3, further comprising a drift stage disposed between the resonance acceleration cavity and the circular reflection target and configured to cause the electron beams to self focus.

7. The CT device according to claim 1, further comprising a transmission unit configured to carry the object to be detected to move along the axis of the circular detector array.

8. The CT device according to claim 1, wherein the angle between the normal of the target surface of the circular reflection target and the incident direction of the electron beams is larger than 90 degrees.

9. The CT device according to claim 1, further comprising a collimator configured to collimate the X-rays.

10. The CT device according to claim 1, wherein each detection unit in the circular detector array is a multi-detector row unit.

11. A method of a CT device comprising steps of
generating electron beams from an electron gun;
deflecting the electron beams with a deflection direction varying as time so as to implement a circular scanning;
restricting the electron beams by a restrictor that has a plurality of circularly distributed holes, so that when the electron beams scan along the circularly distributed holes, a plurality of electron beams that are distributed circularly are output;
generating X-rays that intersect an axis of the circularly distributed electron beams by the electron beams bombarding the circular reflection target; and
detecting X-rays that have passed through an object to be detected.

12. The method according to claim 11, further comprising a step of accelerating the circularly distributed electron beams in sequence by a resonance acceleration cavity that operates in TM010 mode.

13. The method according to claim 11, further comprising a step of feeding, by a coupler, microwaves generated by a microwave power source to the resonance acceleration cavity to accelerate the electron beams in sequence.

14. The method according to claim 11, further comprising a step of driving the restrictor to move to and fro a certain degree when generating the electron beams, the degree being less than or equal to the angle between two lines, one line connecting one of the holes on the restrictor to a center of a circle on which the circularly distributed holes are positioned, the other line connecting an adjacent hole to the center.

* * * * *